United States Patent [19]

Newson et al.

[11] 4,096,244
[45] Jun. 20, 1978

[54] IMMUNOGLOBULINS FOR ADMINISTRATION TO PIGLETS

[75] Inventors: Freeman Oswald Newson, Toronto; Michael Charles Attwell, Islington, both of Canada

[73] Assignee: Canada Packers Limited, Toronto, Canada

[21] Appl. No.: 696,869

[22] Filed: Jun. 16, 1976

[30] Foreign Application Priority Data

Jun. 20, 1975    Canada .................................. 229842

[51] Int. Cl.² ...................... A61K 39/00; A61K 35/16
[52] U.S. Cl. ........................................ 424/85; 424/86; 424/87; 424/101; 426/647
[58] Field of Search ...................... 424/85, 86, 87, 101

[56] References Cited

U.S. PATENT DOCUMENTS

| | | | |
|---|---|---|---|
| 914,644 | 3/1909 | Deutschmann ........................ | 424/85 |
| 1,264,285 | 4/1918 | Dorset et al. ........................ | 424/85 |
| 2,607,716 | 8/1952 | Link ........................................ | 424/85 |

*Primary Examiner*—Sam Rosen
*Attorney, Agent, or Firm*—Hirons & Rogers

[57] ABSTRACT

Immunoglobulins for new-born piglets to provide them with antibodies effective against disease are administered as a dried particulate serum obtained from animal blood and having a reduced sodium chloride content. Such a serum is palatable to piglets and can be orally administered along with feed-stuffs.

8 Claims, No Drawings

IMMUNOGLOBULINS FOR ADMINISTRATION TO PIGLETS

FIELD OF THE INVENTION

This invention relates to animal blood serum compositions and methods for their preparation. More particularly, it relates to animal blood serum compositions suitable for administration to newborn piglets, and to processes for improving the health of newborn piglets.

BACKGROUND OF THE INVENTION

One of the major defence mechanisms of animals against pathogenic organisms consists of the presence of antibodies in the tissues and fluids of the animal. These antibodies are proteins, normally referred to as immunoglobulins or gammaglobulins, which react specifically with antigens such as pathogenic organisms and their metabolic products.

An animal such as a piglet is born lacking antibodies. It receives its protection by ingesting colostrum, (which contains appreciable quantities of antibodies), normally from the mother. These colostral antibodies represent the animal's protection against disease until it develops its own antibody generating system, which in piglets does not normally start until the animal is at least ten days old. Until the animal is a few days old and has ingested significant amounts of antibodies e.g. from colostrum, the animal has little or no defense against invading pathogenic organisms.

In the case of piglets, it frequently occurs in normal farm practice that newborn piglets do not receive any or sufficient immunoglobulins. Swine litters tend to be large, often larger than the sow can nurse. Off-spring of agalactic sows will receive no colostrum from the mother. Also of course, the sow may die during farrowing. In all such cases, the piglet is extremely vulnerable to contracting infectious disease, especially scours. Pig scours are a major factor in the heavy losses of piglets in the period between birth and weaning (about six weeks old), which losses are estimated to be as high as 20% of all newborn piglets.

In addition, attempts are being made to improve the economics of raising pigs, by reducing or eliminating the weaning period. Such a zero-weaning operation can substantially increase the number of offspring per year which a sow can produce. In all such cases, however, it is necessary to provide the piglets with an alternative source of immunoglobulins during the first few days after birth.

BRIEF DESCRIPTION OF THE PRIOR ART

It is known to obtain an immunoglobulin fraction from porcine blood and to administer such a fraction to newborn piglets. Whilst this procedure has proved effective to some extent, it is not practical from an economic point of view. The immunoglobulin amounts required by a piglet, especially during its first day, are high, and fractionation of porcine blood to obtain a fraction sufficiently concentrated in active immunoglobulin on a large scale is economically unattractive. Further, an isolation and fractionation process has to be adopted which will not deactivate the immunoglobulins, and such processes are tedious and uneconomic.

Accordingly, there is a need in the field of pig breeding and raising for a new process whereby large amounts of immunoglobulins can be produced without denaturation and in an economically attractive manner, for simple and convenient administration to piglets in the necessary amounts to confer protection against infection.

SUMMARY OF THE INVENTION

It is therefore an object of the present invention to provide a composition containing active immunoglobulins which is suitable for administration to newborn piglets.

It is a further object of the present invention to provide a process for protecting newborn piglets against invading pathogenic organisms.

The present invention is based upon the discovery that the required immunoglobulins can be administered to piglets, to provide the necessary protection against pathogenic organisms, by feeding the piglets animal blood serum in which the saline content has been reduced. The saline reduced serum can be fed orally to the piglets, in the necessary dosages, by mixing it with other feed materials.

Thus according to the present invention, there is provided a dried particulate serum obtained from animal blood, said serum containing active immunoglobulins and being of reduced saline content, and being acceptable to and palatable to newborn piglets for oral administration thereto.

According to another aspect of the invention, there is provided a process for preparing a dried particulate serum containing active immunoglobulins, which comprises the steps of:

treating animal blood to separate from it cellular materials and fibrinogen so as to obtain liquid serum;

at least partially desalinating this serum;

and drying the serum to convert it to a particulate form.

According to a further aspect of the invention, there is provided a process for protecting newborn piglets against invading pathogenic organisms, which comprises orally feeding to piglets an effective antibody providing amount of a dried particulate serum obtained from animal blood, said serum containing active immunoglobulins and being of reduced saline content.

An important feature of the present invention is the reduction of the saline content of the blood serum. Previous attempts to feed blood serum to piglets have been unsuccessful, because the piglets simply will not eat it. Administration by means involving injection is to be avoided, since immunoglobulins administered this way are not effective in protecting the piglet against infection. For best results, the immunoglobulins should be present in the animal's gastro-intestinal tract, and this is achieved by oral feeding of the immunoglobulins to the animal. The present invention is based upon the surprising discovery that, if the saline content of the serum is reduced to 3% or less, on a solids basis, the serum is acceptable to newborn piglets even in the comparatively large amounts they require in the first day of life in order to obtain a sufficient quantity of immunoglobulins for their protection.

DESCRIPTION OF THE PREFERRED EMBODIMENTS

Whilst it is preferred in the present invention to use serum obtained from porcine blood, bovine and other animal blood serum may also be used, although they are apparently somewhat less effective in conferring the necessary degree of protection.

The serum used in the present invention is obtained from pooled blood collected from a large number of Government-inspected slaughtered animals such as swine or cattle. Normally, the pooled blood is thoroughly mixed with an anticoagulant solution, e.g. sodium citrate solution, sodium oxalate solution or sodium phosphate solution, to prevent premature coagulation or clotting. Then the blood is centrifuged to separate cellular materials from the plasma. The serum is obtained from plasma by known means, initiated by addition of calcium ions. The calcium ions in effect counteract the anticoagulant previously added, so that on standing for a period of time (e.g. about two hours) clot formation occurs as the fibrinogen is converted to fibrin, and the fibrin-clot is removed to give the serum.

In an alternative process, the serum can be obtained by initially allowing the blood to clot, i.e., omitting the addition of the anticoagulant. Then the clotted mass is removed, so as to obtain the serum.

Porcine or bovine serum so obtained is generally a clear or reddish tinged liquid, and contains about 1% of sodium chloride, and contains in the region of 7–10% by weight of proteins, of which about 1/5th is immunoglobulins. It is next necessary according to the invention to reduce this salt content. This is conveniently achieved by dialysis, e.g. through a membrane, against cold water. Alternative methods which can be used to reduce the salt content include ion exchange, ultrafiltration, gel filtration, solvent precipitation, electrodialysis and reverse osmosis, all of which are methods known in the chemical processing art.

Then the desalinated serum is dried and converted to a free-flowing powdered form. Any drying method which does not deactivate the immunoglobulins in the serum can be adopted. Preferred methods are freeze drying and spray drying. Then the dried serum is ready for oral administration to the piglets.

If desired, the serum, before or after drying, can be mixed with other materials to be fed to the piglets, such as antibiotics, nutrients and mineral feed supplements. The serum powder, with or without additives, is suitably shipped to the animal feeding station to be mixed with the feed-stuff prior to feeding to the piglets. The serum powder is stable over substantial periods of time, and can be transported and mixed without difficulty and without significant risk of its deactivation.

Typically, the dried serum powder of the present invention has a nitrogen content, as determined by the Kjeldahl method, of from about 13 to about 15% by weight, the nitrogen being present as protein, and a sodium chloride content of from about 0.2 to about 1.5 weight percent, the balance of the serum powder comprising other materials such as other inorganic residues, in small amounts. Of the protein content, about 15-22 weight percent constitutes immunoglobulins.

It has been found that, on its first day of life, a piglet needs to obtain about 10 grams of pure immunoglobulin per kilogram body weight. An average piglet of body weight about 1½ kilograms thus needs about 15 grams of pure immunoglobulin, which means it must eat from about 50 to about 100 grams of dried serum, which is a substantial amount. It has been found that, unless the sodium chloride content of the dried serum is low, e.g. below about 3% by weight, the feed containing it is unpalatable and will not be ingested by the piglets. Unless steps are taken to desalinate the serum, the resulting dried serum will contain about 10–15% sodium chloride and will not be taken orally by the piglets, so that it is useless for providing the piglets with active immunoglobulin for defence against infection.

It is of course necessary that any other ingredients mixed with the dried serum for oral administration to piglets, such as feedstuffs, antibiotics, vitamins and other nutrients, also be low in sodium chloride content, in order to produce a foodstuff of overall palatability to the piglets. However, most if not all of the materials commonly fed to piglets during the first few days of life meet this criterion.

Feedstuffs for newborn piglets, with which the dried serum of the present invention may be mixed, are in accordance with those known and previously administered. For the first 24 hours of the piglet's life, the feedstuff commonly comprises sugar-rich materials, for example dextrose, and vegetable oils, such as corn oil, in roughly equal proportions, in admixture with water. In formulations in which the dried serum of the present invention is used, for this first day of feeding, it is preferred to prepare and administer a feed composition comprising an aqueous mixture the solids content of which comprises from about 50 to about 60 percent by weight of the dried serum, and from about 40 to about 50% by weight of feedstuff containing a mixture of carbohydrate and vegetable oil, the aqueous mixture containing from about 0.2 to about 1% by weight of sodium chloride. Minerals, vitamins and antibiotics may also be added, in very small amounts. For the second and subsequent days, it is preferred to prepare a feed composition comprising a mixture of basic milk powder (95–98% by weight), vitamins, minerals and choline chloride, as a 20% solids solution in water, and to mix this solution with dried serum in the proportion of about 100 parts by weight of said aqueous solution to about 15–25 parts by weight of dried serum. Thus the serum is used in an amount of from about 75 to about 125 parts by weight per 100 parts by weight of the basic milk powder. During the 2nd–10th day of life, a piglet normally needs from about 1 gm. to about 3 gm. of active immunoglobulins, per kilogram of body weight, correspondong to about 5g to about 20g of dried serum, per day.

As noted, the process of preparing the dried serum of the present invention is very simple, involving separation of the serum from blood, partial salt removal and drying. It is a much simpler process than the isolation of an immunoglobulin rich fraction from animal blood, and is hence much more economical to operate on a large scale. A further advantage of the present invention is that the resultant dried serum contains appreciable quantities of other proteins, especially albumin, which are nutritious to the piglets.

The invention is further described in the following examples

EXAMPLE 1

Hog blood (250 liters) was collected from freshly-killed, healthy, inspected hogs and mixed with an anticoagulant solution of 20% aqueous sodium citrate (300 ml/1.5 gal blood). The blood was centrifuged to remove the red blood cells. Calcium chloride (1.0 kg) was added to the plasma (127 liters). Clotting started within 10–15 minutes. The mixture was stirred for 1 hour, and then it was refrigerated overnight. The precipitate (i.e. fibrin) was removed by filtration through a stainless steel screen. The porcine serum obtained (113 liters) was shown by analysis to contain about 8.2% protein (by Biuret), of which by electrophoresis about 20% was immunoglobulins.

The serum was partially desalinated by dialysis as follows: The serum was added to 3¼ inch diameter dialysis tubing (seamless regenerated cellulose), which after sealing was placed in a tank (100-gallon capacity) of tap water. Fresh tap water was fed into the tank continuously at a rate of approximately 2 gallons per minute. The salt content of the serum was monitored by conductivity measurements, and the dialysis was continued until the conductivity had been reduced to about 80–90% of the initial reading. The conductivity before and after 45 hours of dialysis was 15 and 1.6 millimhos respectively.

The resulting dialyzed slurry (123 liters) was freeze dried to yield 8.58 kilograms of pale reddish-brown immunoglobulin powder. Analysis showed that the powder contained 13.2% nitrogen (as protein) by the Kjeldahl method, and 1.3% sodium chloride (based on sodium content). By electrophoresis, it was shown that the protein component comprised 21% gammaglobulins (immunoglobulins), 45% albumin, and 34% other proteins (mainly $\alpha$-and $\beta$-globulins).

Portions of the dried serum so prepared were mixed with feedstuff in the following formulation to provide a first-day feed formulation:

dried serum 63.1g;
dextrose 25g;
corn oil 25g;
carboxymethyl cellulose 0.5g;
water to make a total volume of 300mls.

The composition was prepared by homogenizing for 30 seconds in a Polytron (Trademark) homogenizer. One cc of trace mineral composition (containing copper, iron, manganese and zinc ions) and 1 cc of mixed vitamin composition, containing vitamins A, D, E, was also added.

A subsequent days feed formulation was prepared of the following composition:

Basic milk powder 97kg;
Vitamin mix 1kg;
Mineral mix 1kg;
Choline chloride mix 1kg;
Water to form a 20% solids content solution.

The basic milk powder contained about 77% low temperature skim milk-fat pre-mix (40% ether extract, 23% crude protein) about 8% low temperature skim milk powder (containing 34.5% crude protein), about 5% buttermilk powder, about 10% Nutricase (Trademark) (purified casein product) and 0.25% sodium chloride as iodized salt. Groups of newborn piglets were selected and orally fed with the above compositions. For the first day, the piglets in the experimental groups were fed with the above first day feed formulation, each piglet being given 12 feedings of 25 cc portions of the formulation at two hour intervals.

For the 2nd–10th day, each piglet was orally fed with subsequent days feed formulation in an amount of 5% of the body weight of the piglet of the solution in admixture with an amount of the dried serum sufficient to provide approximately 2g of immunoglobulins per kg body weight of the piglet. For the 11th to the 21st day, the piglets are fed the same subsequent day's feed formulation but omitting the dried serum. In the control groups, the same feeds were administered in the same amounts, but omitting the dried serum. The results, expressed as the number of survivals of piglets in the various groups, are given below in Table 1. The various groups 1, 2 and 3 were reared under different farm conditions and at different locations. In group 1, the piglets were born somewhat prematurely by Caesarean section. In groups 2 and 3, the piglets were natural born. Negative controls, in which substantial numbers (over 100) of newborn piglets in two groups were fed with the same feed formulations in the same amounts, but omitting any immunoglobulins, showed an average survival after 21 days of about 15%.

TABLE 1

| Group | No. of Pigs Birth | 3 Weeks | % Survival |
|---|---|---|---|
| Control #1 | 7 | 1 | 14.3 |
| Experimental #1 | 7 | 4 | 57.1 |
| Control #2 | 8 | 0 | 0 |
| Experimental #2 | 8 | 7 | 88 |
| Experimental #3 | 8 | 6 | 75 |
| Experimental #4 (duplicate of Experimental #3) | 8 | 7 | 88 |

EXAMPLE 2

Phosphated beef plasma (70 lb) obtained by centrifugation of blood from healthy, inspected cattle was defibrinated as in Example 1 by adding calcium chloride (0.35lb). The serum obtained (60 lb) after removal of the fibrin was dialyzed against tap water as described in Example 1. The conductivity of the serum before and after dialysis was 16 and 1.2 millimhos respectively. The dialyzed serum (63lb) was freeze dried to give 1300 grams of beige immunoglobulin powder. Analysis showed the powder contained 14.0% nitrogen (as protein) by Kjeldahl method. By electrophoresis, the protein was shown to be composed of 18.4% immunoglobulins, 15.0% $\alpha$-globulins, 7.0% $\beta$-globulins, and 59.7% albumin.

This dried serum was mixed into a first day feed composition and a subsequent days feed composition, and administered to piglets, newly born prematurely by Caesarean section as described in Example 1. The results are given in Table 2.

TABLE 2

| Group | No. of Pigs Birth | 3 Weeks | % Survival |
|---|---|---|---|
| Control #1 | 7 | 1 | 14.3 |
| Experimental | 8 | 5 | 62.5 |

We claim:

1. A dried particulate porcine or bovine blood serum, said serum containing active immunoglobulins and having a sodium chloride content of less than about 3% by weight, and being acceptable to and palatable to newborn piglets for oral administration thereto as a feed stuff component, so as to confer on the piglets increased protection against infection.

2. The serum of claim 1 which comprises a nitrogen content, as determined by the Kjeldahl method, of from about 13 to about 15% by weight, the nitrogen being present as protein, and a sodium chloride content of from about 0.2 to about 1.5 weight percent.

3. A feed composition for administration to piglets less than 24 hours old, said composition consisting essentially of an aqueous mixture the solids content of which comprises from about 50 to about 60 weight percent of dried particulate serum as claimed in claim 1 and from about 40 to about 50 weight percent of a mixture of carbohydrate and vegetable oil.

4. A feed composition for administration to piglets at least 24 hours old, said composition consisting essentially of an aqueous mixture of dried particulate serum as claimed in claim 1, and basic milk powder, said serum being present in an amount of from about 75 to about 125 parts by weight, per 100 parts by weight of the basic milk powder.

5. A process for preparing a dried particulate serum containing active immunoglobulins, which comprises the steps of: treating animal blood to separate from it cellular materials and fibrinogen so as to obtain liquid serum; at least partially desalinating the serum to reduce the sodium chloride content to less than about 3% by weight on a dry basis; and drying the serum to convert it to a particulate form.

6. The process of claim 5 wherein the animal blood is bovine blood.

7. The process of claim 5 wherein the animal blood is porcine blood.

8. A process for protecting piglets of age less than 10 days against the effects of invading pathogenic organisms, which comprises orally administering to such piglets a feed material comprising a dried particulate serum obtained from animal blood, said serum containing active immunoglobulins and having a sodium chloride content of less than about 3% by weight, in admixture with piglet acceptable feed stuffs.

* * * * *